(12) United States Patent
Bar-Tal et al.

(10) Patent No.: US 12,402,948 B2
(45) Date of Patent: Sep. 2, 2025

(54) USING A PREDETERMINED ABLATION-CURRENT PROFILE

(71) Applicant: BIOSENSE WEBSTER (ISRAEL) LTD., Yokneam (IL)

(72) Inventors: Meir Bar-Tal, Haifa (IL); Yigal Ultchin, Rehovot (IL); Abraham Berger, Givatayim (IL); Avri Hazan, Givatayim (IL); Assaf Rubissa, Misgav (IL); Alaa Zoubi, Sakhnin (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1112 days.

(21) Appl. No.: 17/352,053

(22) Filed: Jun. 18, 2021

(65) Prior Publication Data

US 2021/0315641 A1 Oct. 14, 2021

Related U.S. Application Data

(62) Division of application No. 15/987,160, filed on May 23, 2018, now Pat. No. 11,065,058.

(51) Int. Cl.
*A61B 18/12* (2006.01)
*A61B 18/14* (2006.01)
(Continued)

(52) U.S. Cl.
CPC .......... *A61B 34/10* (2016.02); *A61B 18/1206* (2013.01); *A61B 18/1492* (2013.01);
(Continued)

(58) Field of Classification Search
CPC ............ A61B 18/1206; A61B 18/1233; A61B 18/1492; A61B 2018/00577;
(Continued)

(56) References Cited

U.S. PATENT DOCUMENTS 4,016,117 A 4/1977 Griffin
4,931,488 A 6/1990 Chiquet
(Continued)

FOREIGN PATENT DOCUMENTS

CA 2106408 A1 5/1993
EP 3158961 A1 4/2017

OTHER PUBLICATIONS

Juan A. Lopez-Molina et al: "Assessment of Hyperbolic Heat Transfer Equation in Theoretical Modeling for Radiofrequency Heating Techniques", The Open Biomedical Engineering Journal, vol. 2, No. 1, Apr. 18, 2008 (Apr. 18, 2008), pp. 22-27 (Copy Provided).

(Continued)

*Primary Examiner* — Michael F Peffley
*Assistant Examiner* — Amanda L Zink
(74) *Attorney, Agent, or Firm* — Clayton, McKay & Bailey, PC

(57) ABSTRACT

Described embodiments include a system that includes a current source generator and a processor. The processor is configured to drive the current source generator to supply, for application to tissue of a subject, an electric current having an amplitude that varies in accordance with a predefined function of time, such that the amplitude initially monotonically increases to a maximum value. Other embodiments are also described.

20 Claims, 3 Drawing Sheets

(51) Int. Cl.
*A61B 34/10* (2016.01)
*G16H 50/50* (2018.01)
*A61B 18/00* (2006.01)
*A61B 90/00* (2016.01)

(52) U.S. Cl.
CPC .... *G16H 50/50* (2018.01); *A61B 2018/00577* (2013.01); *A61B 2018/00642* (2013.01); *A61B 2018/00678* (2013.01); *A61B 2018/0072* (2013.01); *A61B 2018/00791* (2013.01); *A61B 2034/104* (2016.02); *A61B 2090/062* (2016.02)

(58) Field of Classification Search
CPC .......... A61B 2018/00642; A61B 2018/00678; A61B 2018/0072; A61B 2018/00791; A61B 2034/104; A61B 2090/062; A61B 34/10

See application file for complete search history.

(56) References Cited

U.S. PATENT DOCUMENTS

| | | | |
|---|---|---|---|
| 5,735,846 | A | 4/1998 | Panescu |
| 6,056,745 | A | 5/2000 | Panescu et al. |
| 6,132,426 | A | 10/2000 | Kroll |
| 6,930,279 | B2 | 8/2005 | Myers |
| 8,267,927 | B2* | 9/2012 | Dalal ............... A61B 34/10 606/41 |
| 8,456,182 | B2 | 6/2013 | Bar-Tal et al. |
| 8,556,891 | B2 | 10/2013 | Mathur |
| 9,241,756 | B2 | 1/2016 | Berger et al. |
| 9,265,574 | B2 | 2/2016 | Bar-tal et al. |
| 9,532,828 | B2 | 1/2017 | Condie et al. |
| 10,206,733 | B2 | 2/2019 | Govari et al. |
| 2005/0010206 | A1 | 1/2005 | Nasab et al. |
| 2009/0287205 | A1* | 11/2009 | Ingle ............... A61B 18/14 606/34 |
| 2009/0318804 | A1 | 12/2009 | Avital et al. |
| 2010/0049188 | A1 | 2/2010 | Nelson |
| 2011/0022041 | A1 | 1/2011 | Ingle |
| 2012/0273473 | A1 | 11/2012 | Zhang |
| 2013/0006237 | A1 | 1/2013 | Werner |
| 2013/0345697 | A1 | 12/2013 | Garcia et al. |
| 2014/0201669 | A1* | 7/2014 | Liu ............... A61B 34/10 715/771 |
| 2014/0296842 | A1* | 10/2014 | Mansi ............... A61B 34/10 703/2 |
| 2015/0005758 | A1 | 1/2015 | Berger et al. |
| 2015/0088120 | A1* | 3/2015 | Garcia ............... A61B 18/1477 606/34 |
| 2015/0359603 | A1 | 12/2015 | Levy et al. |
| 2016/0022369 | A1 | 1/2016 | Audigier et al. |
| 2018/0008229 | A1 | 1/2018 | Govari et al. |
| 2018/0228546 | A1* | 8/2018 | Lan ............... A61B 34/10 |
| 2019/0357979 | A1 | 11/2019 | Bar-tal et al. |
| 2020/0196908 | A1* | 6/2020 | Ben-Haim ............... A61B 34/25 |

OTHER PUBLICATIONS

Extended European Search Report received for European Application No. 19179108.6, mailed on Sep. 19, 2019, 6 pages.

Extended European Search Report, received for European Application No. 19175990.1, mailed on Oct. 15, 2019, 11 pages.

Jain et al., "A Three-Dimensional Finite Element Model of Radiofrequency Ablation with Blood Flow and its Experimental Validation", Annals of Biomedical Engineering, vol. 28, No. 9, pp. 1075-1084, 2000.

Koruth et al., "Chamber-Specific Radiofrequency Lesion Dimension Estimation Using Novel Catheter-Based Tissue Interface Temperature Sensing", JACC: Clinical Electrophysiology, vol. 3, No. 10, pp. 1092-1102, 2017.

\* cited by examiner

USING A PREDETERMINED ABLATION-CURRENT PROFILE

CROSS REFERENCE TO RELATED APPLICATIONS

This application claims priority as a division of U.S. patent application Ser. No. 15/987,160 (issued as U.S. Pat. No. 11,065,058), filed May 23, 2018, entitled "Using a Predetermined Ablation-Current Profile," which is incorporated herein by reference as if set forth herein in its entirety.

FIELD OF THE INVENTION

The present invention is related to the field of medical devices and treatments, particularly those associated with the ablation of biological tissue.

BACKGROUND

During some types of ablation procedures, an ablation electrode is brought into contact with the tissue that is to be ablated, and electric currents are then passed through the tissue, causing a lesion to be formed in the tissue.

U.S. Pat. No. 5,735,846 describes systems and methods for ablating body tissue. An electrode contacts tissue at a tissue-electrode interface to transmit ablation energy at a determinable power level. The systems and methods include an element to remove heat from the electrode at a determinable rate. The systems and methods employ a processing element to derive a prediction of the maximum tissue temperature condition occurring beneath the tissue-electrode interface. The processing element controls the power level of ablation energy transmitted by the electrode, or the rate at which the electrode is cooled, or both, based, at least in part, upon the maximum tissue temperature prediction.

U.S. Pat. No. 9,241,756 to Berger et al., whose disclosure is incorporated herein by reference, describes a method for performing a medical procedure, which includes coupling a probe to tissue in an organ of a patient. Ablation energy is applied to the tissue using the probe. A model of an evolution of steam pressure in the tissue, caused by the ablation energy, as a function of time is estimated. Based on the model, an occurrence time of a steam pop event caused by the steam pressure is predicted, and the predicted occurrence time of the steam pop event is indicated to an operator.

U.S. Pat. No. 9,265,574 to Bar-tal et al., whose disclosure is incorporated herein by reference, describes apparatus, consisting of a probe, configured to be inserted into a body cavity, and an electrode having an outer surface and an inner surface connected to the probe. The apparatus also includes a temperature sensor, protruding from the outer surface of the electrode, which is configured to measure a temperature of the body cavity.

Mudit K. Jain and Patrick D. Wolf, "A three-dimensional finite element model of radiofrequency ablation with blood flow and its experimental validation," Annals of Biomedical Engineering 28.9 (2000): 1075-1084, describes a three-dimensional finite element model for the study of radiofrequency ablation. The model was used to perform an analysis of the temperature distribution in a tissue block heated by RF energy and cooled by blood (fluid) flow. The effect of fluid flow on the temperature distribution, the lesion dimensions, and the ablation efficiency was studied.

SUMMARY OF THE INVENTION

There is provided, in accordance with some embodiments of the present invention, a system that includes a current source generator and a processor. The processor is configured to drive the current source generator to supply, for application to tissue of a subject, an electric current having an amplitude that varies in accordance with a predefined function of time, such that the amplitude initially monotonically increases to a maximum value.

In some embodiments, the predefined function of time includes a time series of values.

In some embodiments, the predefined function of time returns, for any value of time t, $(a+t^b)/(c+d*t^e+f*t^g)$ for constants a, b, c, d, e, f, and g.

In some embodiments, the amplitude is a root mean square (RMS) amplitude, and the maximum value of the RMS amplitude is between 0.8 and 1.2 A.

In some embodiments, the processor is configured to cause the amplitude to monotonically increase to the maximum value in less than 0.5 s.

In some embodiments, the processor is further configured to:

during the application of the electric current and following the increase of the amplitude to the maximum value, receive a signal indicating a surface temperature of the tissue, and in response to the signal, adjust the amplitude of the electric current.

In some embodiments, the processor is further configured to calculate an estimated maximum subsurface temperature of the tissue from the surface temperature, and the processor is configured to adjust the amplitude of the electric current responsively to the estimated maximum subsurface temperature.

In some embodiments, the electric current is applied to the tissue by a distal tip of a catheter, and the processor is further configured to:

calculate an estimated depth of penetration into the tissue of the distal tip of a catheter, and select the predefined function of time from multiple predefined functions of time, responsively to the estimated depth of penetration.

There is further provided, in accordance with some embodiments of the present invention, a method that includes loading, from a computer memory, a predefined function of time, and driving a current source generator to supply, for application to tissue of a subject, an electric current having an amplitude that varies in accordance with the predefined function of time, such that the amplitude initially monotonically increases to a maximum value.

There is further provided, in accordance with some embodiments of the present invention, a system that includes a computer memory and a processor. The processor is configured to, while simulating an application of an electric current to simulated tissue, control an amplitude of the electric current such that a maximum subsurface temperature of the simulated tissue increases toward a predefined threshold without exceeding the predefined threshold. The processor is further configured to derive a function of time from values of the amplitude over the simulated application, and to store the function of time in the computer memory for subsequent use in an ablation procedure.

In some embodiments, the processor is configured to, by controlling the amplitude, cause the amplitude to initially monotonically increase to a maximum value.

In some embodiments, the amplitude is a root mean square (RMS) amplitude, and the maximum value of the RMS amplitude is between 0.8 and 1.2 A.

In some embodiments, the processor is configured to cause the amplitude to monotonically increase to the maximum value in less than 0.5 s.

In some embodiments, the processor is configured to, by controlling the amplitude, cause the maximum subsurface temperature to increase to within 5° C. of the predefined threshold in less than 1.5 s from a start of the simulated application, and to then remain within 5° C. of the predefined threshold until an end of the simulated application.

In some embodiments, the processor is configured to derive the function of time by selecting at least some of the values of the amplitude over the simulated application, and to store the function of time by storing the selected values.

In some embodiments, the processor is configured to derive the function of time by fitting a predefined function template to the values of the amplitude over the simulated application.

In some embodiments, the function of time returns, for any value of time t, $(a+t^b)/(c+d*t^e+f*t^g)$ for constants a, b, c, d, e, f, and g.

In some embodiments, the processor is configured to control the amplitude by, given a current amplitude-value A of the amplitude and a current temperature-value T of the maximum subsurface temperature, setting a next value of the amplitude to $\min(A, \max(A_{min}, |A_{min}-C*(T-T_{lim})|))$, where $A_{min}$ is a predefined minimum amplitude value, C is a predefined constant, and $T_{lim}$ is the predefined threshold.

In some embodiments, the processor is configured to cause the maximum subsurface temperature to increase asymptotically toward the predefined threshold by controlling the amplitude.

In some embodiments,
the electric current is a simulated electric current,
the amplitude is a simulated amplitude,
the system further includes a current source generator, and
the processor is further configured to drive the current source generator to supply an actual electric current having an actual amplitude that varies in accordance with the function of time during the ablation procedure.

In some embodiments, the predefined threshold is between 120 and 130° C.

There is further provided, in accordance with some embodiments of the present invention, a method that includes, using a processor, while simulating an application of an electric current to simulated tissue, controlling an amplitude of the electric current such that a maximum subsurface temperature of the simulated tissue increases toward a predefined threshold without exceeding the predefined threshold. The method further includes deriving a function of time from values of the amplitude over the simulated application, and storing the function of time for subsequent use in an ablation procedure.

The present invention will be more fully understood from the following detailed description of embodiments thereof, taken together with the drawings, in which:

DETAILED DESCRIPTION OF EMBODIMENTS

Overview

In general, it is desirable that an ablation procedure proceed as quickly as possible. However, applying a large amount of power to the tissue within a short interval of time may cause the subsurface temperature of the tissue to become too high, such that dangerous steam pops may form within the tissue. One solution is to estimate the subsurface temperature during the procedure, as described, for example, in the aforementioned U.S. Pat. Nos. 9,241,756 and 9,265,574. However, in some cases, this solution may be difficult to implement effectively.

To address this challenge, embodiments of the present invention utilize, for the procedure, a predetermined ablation-current profile that is known to safely deliver a large amount of power within a small interval of time. To generate the profile, a processor simulates the effect of an ablation current on the subsurface temperature of the tissue. In particular, the processor computes a time-varying current amplitude that causes the maximum subsurface temperature of the tissue to quickly approach a maximum allowable temperature value $T_{lim}$, and then continue to approach $T_{lim}$, or at least remain near $T_{lim}$, without exceeding $T_{lim}$. Subsequently, during the procedure, the processor drives a generator to generate an ablation current in accordance with the profile.

In each ablation-current profile, the amplitude of the current initially increases rapidly to a relatively large maximum value. This initial burst of current causes the maximum subsurface temperature to quickly approach $T_{lim}$, as described above. Subsequently, after an optional plateau at the maximum value, the amplitude decreases measuredly from the maximum value, such that the maximum subsurface temperature does not exceed $T_{lim}$.

In general, during an ablation procedure, the temperature of the tissue increases as a function of the density of the current that is applied to the tissue. Hence, embodiments described herein typically use a current source generator, such that the applied current density does not vary with any changes in the impedance of the tissue that may occur as the tissue is heated. In contrast, were a power source generator used, the applied current density might vary with changes in the tissue impedance, leading to unexpected changes in the temperature of the tissue.

System Description

Figure 1:
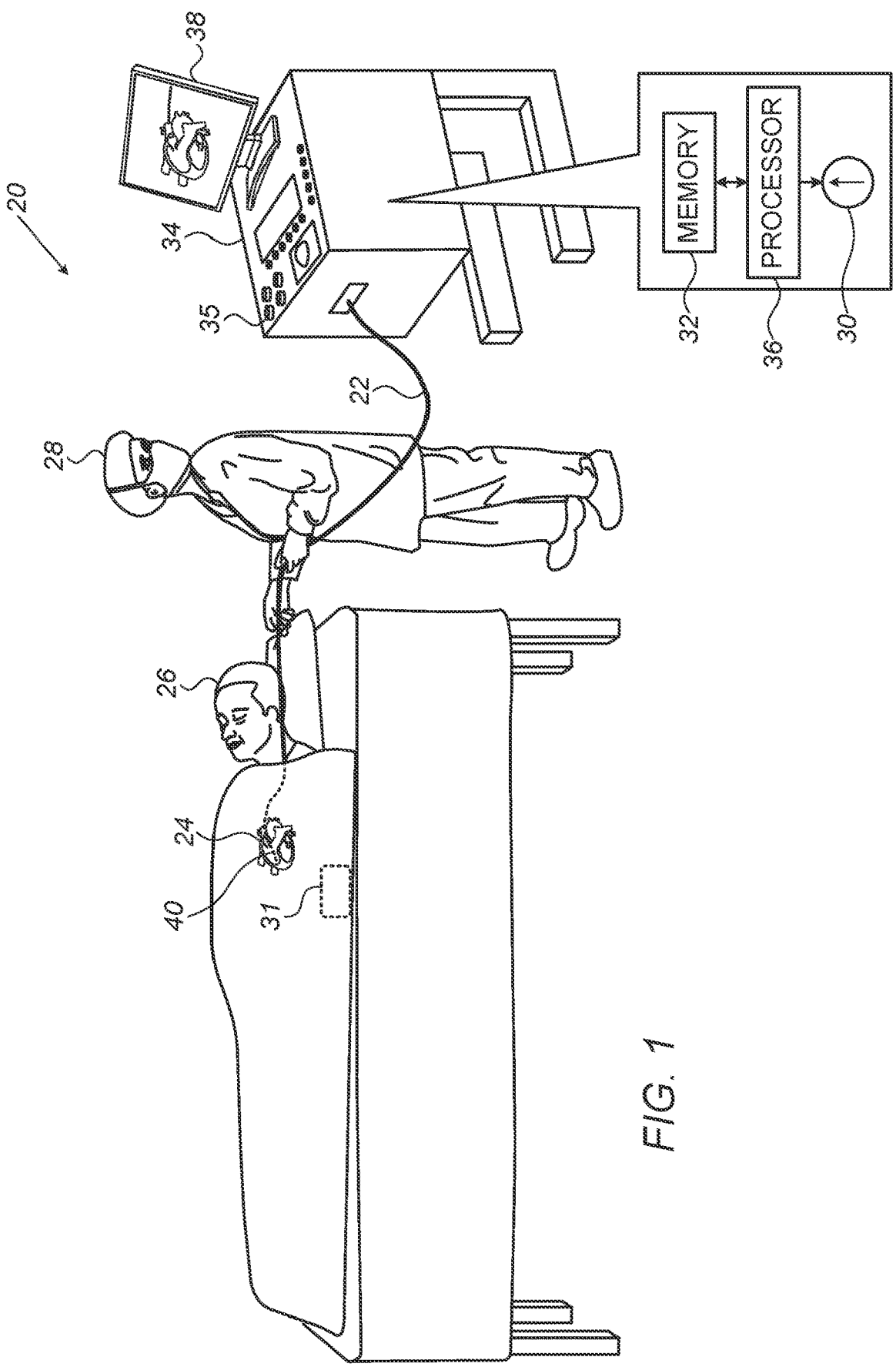
FIG. 1 is a schematic illustration of a system for ablating tissue of a subject, in accordance with some embodiments of the present invention.

Reference is initially made to FIG. 1, which is a schematic illustration of a system 20 for ablating tissue of a subject 26, in accordance with some embodiments of the present invention.

FIG. 1 depicts a physician 28 performing an ablation procedure on subject 26, using an ablation catheter 22. In this procedure, physician 28 first inserts the distal tip 40 of catheter 22 into the subject, and then navigates distal tip 40 to the tissue that is to be ablated. For example, the physician may advance the distal tip through the vasculature of the subject until the distal tip is in contact with tissue located within the heart 24 of the subject. Next, the physician instructs a processor 36 to apply an electric current to the tissue. In response to this instruction, processor 36 loads a predetermined electric-current profile, which specifies an electric-current amplitude as a function of time, from a computer memory 32. Processor 36 then drives a current source generator 30 to supply an electric current having an amplitude that varies in accordance with the function of time. The electric current runs through catheter 22 to distal tip 40, and then passes through the tissue that contacts distal tip 40. For example, in a unipolar ablation procedure, the electric current may pass between one or more electrodes on distal tip 40 and a neutral electrode patch 31 that is coupled externally to the subject, e.g., to the subject's back.

Typically, catheter 22 is connected to a console 34, which contains processor 36, memory 32, and generator 30. Console 34 comprises a user interface, comprising, for example, a keyboard, a mouse, and/or specialized controls 35, which may be used by physician 28 to provide input to processor 36. Alternatively or additionally, during the procedure, physician 28 may use a foot pedal to issue instructions to processor 36. In some embodiments, system 20 further comprises a display 38, and processor 36 causes display 38 to display relevant output to physician 28 during the procedure.

Processor 36 may be connected to memory 32 over any suitable wired or wireless interface, over which the processor may store information to, or retrieve information from, the memory. Such information may include, for example, specifications for an electric-current profile, described below with reference to FIG. 2. Memory 32 may comprise any suitable type of computer memory, such as, for example, a hard drive or flash drive.

Similarly, processor 36 may be connected to generator 30 over any suitable wired or wireless interface, over which the processor may communicate instructions to generator 30, e.g., such as to cause the generator to generate an electric current that tracks a predefined electric-current profile.

Typically, multiple profiles, for different respective sets of ablation parameters, are stored in memory 32. Prior to the application of the electric current to the tissue of the subject, the processor receives or calculates the relevant parameters, and then selects, from the multiple profiles, the profile that corresponds to these parameters.

One such parameter is the thickness of the tissue. In general, for thicker tissue, less current is required to attain a given increase in temperature, relative to thinner tissue. In some embodiments, an estimation of this parameter is input manually by a user. Alternatively, an ultrasound transducer within distal tip 40 may acquire an ultrasound image of the tissue, and the processor may then ascertain the thickness of the tissue from the image, as described, for example, in US 2018/0008229, whose disclosure is incorporated herein by reference.

Another relevant parameter is the flow rate of the irrigation fluid that is passed from the distal tip. In general, as the flow rate increases, more heat is evacuated from the tissue, such that more current is required to achieve a given increase in temperature.

Other relevant parameters include the force with which distal tip 40 contacts the tissue, and the penetration depth of the distal tip, which depends on this force. (In the context of the present application, including the claims, the catheter tip is said to "penetrate" the tissue if the catheter tip presses the surface of the tissue inward. The distance by which the surface is pressed inward is referred to as the penetration distance or penetration depth.) In general, as the penetration depth increases, a greater proportion of the ablation current passes through the tissue rather than through the blood, such that less current is required to achieve a given increase in temperature.

In some embodiments, a force sensor at distal tip 40 measures the contact force, and the processor then calculates an estimated penetration depth of distal tip 40 responsively to this force measurement. Alternatively or additionally, a temperature sensor at distal tip 40 may measure the temperature at the distal tip, and the processor may then calculate the penetration depth responsively to this temperature measurement. Alternatively or additionally, an impedance may be measured between the distal tip and a reference electrode that is coupled externally to the subject, and the processor may then calculate the penetration depth responsively to this impedance measurement.

For example, to estimate the penetration depth, the processor may use any of the techniques described in U.S. Pat. No. 9,241,756 to Berger et al. and U.S. Pat. No. 9,265,574 to Bar-tal et al., whose respective disclosures are incorporated herein by reference. Per one such technique, the processor first estimates the penetration depth of the distal tip using the aforementioned impedance and force measurements, and then re-estimates this depth until a match is found between these measurements and the temperature and impedance values calculated by a finite element model.

In general, processor 36 may be embodied as a single processor, or as a cooperatively networked or clustered set of processors. In some embodiments, the functionality of processor 36, as described herein, is implemented solely in hardware, e.g., using one or more Application-Specific Integrated Circuits (ASICs) or Field-Programmable Gate Arrays (FPGAs). In other embodiments, the functionality of processor 36 is implemented at least partly in software. For example, in some embodiments, processor 36 is embodied as a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Using an Electric-Current Profile

Figure 2:
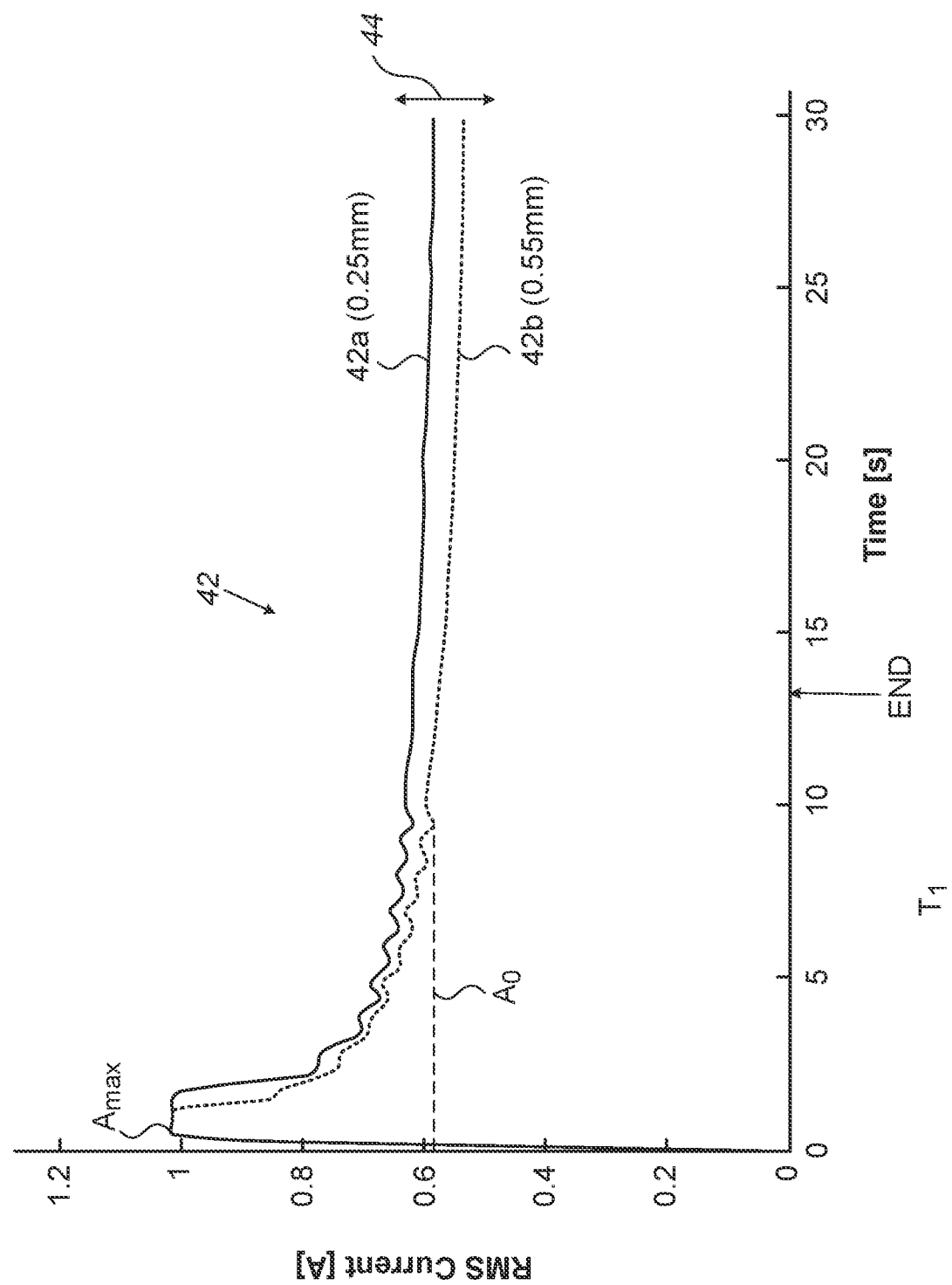
FIG. 2 is a schematic illustration of two electric-current profiles, in accordance with some embodiments of the present invention.

Reference is now made to FIG. 2, which is a schematic illustration of two electric-current profiles 42, in accordance with some embodiments of the present invention.

By way of example, FIG. 2 shows two profiles 42 that were generated using the simulation techniques described below with reference to FIG. 3: a first profile 42a, corresponding to a penetration depth of 0.25 mm and a tissue thickness of approximately 4 mm, and a second profile 42b, corresponding to a penetration depth of 0.55 mm and a tissue thickness of approximately 4 mm. As noted above, by controlling the current source generator, the processor may cause the electric current that is generated by the generator and applied to the subject to track either one of these profiles.

Since the currents used for ablation are typically alternating currents (e.g., at radiofrequencies), FIG. 2 plots the root mean square (RMS) amplitude of the currents, and portions of the description below similarly refer to the RMS amplitude, per the convention in the art. It is noted, however, that a current profile may alternatively be defined in terms of the peak amplitude of the current, or any other suitable measure of amplitude.

As shown in FIG. 2, the RMS amplitude of the current initially increases, typically (but not necessarily) monotonically, to a relatively high maximum value $A_{max}$, which is, for example, between 0.8 and 1.2 A. Typically, this initial increase in amplitude is as rapid as generator 30 allows; thus, for example, the amplitude may increase to $A_{max}$ in less than 0.5 s. Subsequently, the amplitude remains at or below $A_{max}$ until the end of the application of the current. For example, the amplitude may plateau at $A_{max}$ (or at least remain within less than 1% of $A_{max}$) for a particular interval of time, before decreasing over time (with the possible exception of one or more small intermittent increases), such that the amplitude remains below the maximum value until the end of the application of the current.

For example, following the plateau at $A_{max}$, the amplitude may decrease to a lower value $A_0$ that is between 50% and 70% of $A_{max}$, and then remain relatively constant over the "tail" portion of the profile, such that, for example, the amplitude remains within ±10% of $A_0$. In general, a deeper penetration of the distal tip of the catheter facilitates greater efficiency in heating the tissue. Hence, the amplitude $A_0$ generally decreases with increase of the penetration depth, as can be observed by comparing first profile 42a to second profile 42b.

Advantageously, during the application of the electric current, it may not be necessary to receive or process any information from the distal tip of the catheter. Rather, the generated electric current may simply track the predefined profile until the physician instructs the processor, at any suitable moment in time, to terminate the application of current, as indicated in FIG. 2 by an "END" indicator. In general, the physician may set the duration of the application of current in accordance with the desired width and/or depth of the lesion, as further described below with reference to FIG. 3. Alternatively, the generated electric current may track the predefined profile for a predetermined interval of time. Such an interval may have a duration of, for example, between 3 and 30 s, such as between 10 and 20 s.

Notwithstanding the above, in some embodiments, the processor may deviate from the predefined profile, in response to feedback received during the procedure. For example, during the application of the electric current and following the increase of the amplitude to the maximum value, the processor may receive one or more signals that indicate a surface temperature of the tissue. (Such signals may be received, for example, from one or more temperature sensors, such as thermocouples, disposed at distal tip 40.) In response to these signals, the processor may adjust the amplitude of the electric current, e.g., by adjusting the amplitude of the tail of the profile, as indicated in FIG. 2 by a double-sided arrow 44. For example, in response to receiving a surface temperature reading that is higher than expected, the processor may lower the amplitude of the current, to avoid overheating the tissue. Conversely, in response to receiving a surface temperature reading that is lower than expected, the processor may raise the amplitude of the current.

In some embodiments, the processor calculates an estimated maximum subsurface temperature of the tissue from the surface temperature, and adjusts the amplitude of the electric current responsively to the estimated maximum subsurface temperature. For example, if the electric-current profile is configured to maintain the maximum subsurface temperature below 120° C., but the processor calculates a maximum subsurface temperature that is greater than 120° C., the processor may reduce the amplitude of the electric current to below the amplitude that is dictated by the electric-current profile.

To estimate the maximum subsurface temperature, the processor may use any of the techniques described in U.S. Pat. No. 9,241,756 to Berger et al. and U.S. Pat. No. 9,265,574 to Bar-tal et al., whose respective disclosures are incorporated herein by reference. For example, the processor may evaluate a finite element heat transfer model of the catheter and tissue environment. The boundary conditions for the model may include the measured surface temperature, the estimated tip penetration depth, and the amplitude of the ablation current. The processor may further incorporate the influence of irrigation by setting a convection boundary condition, using, for example, a computational fluid dynamic (CFD) model.

Generating an Electric-Current Profile

Figure 3:
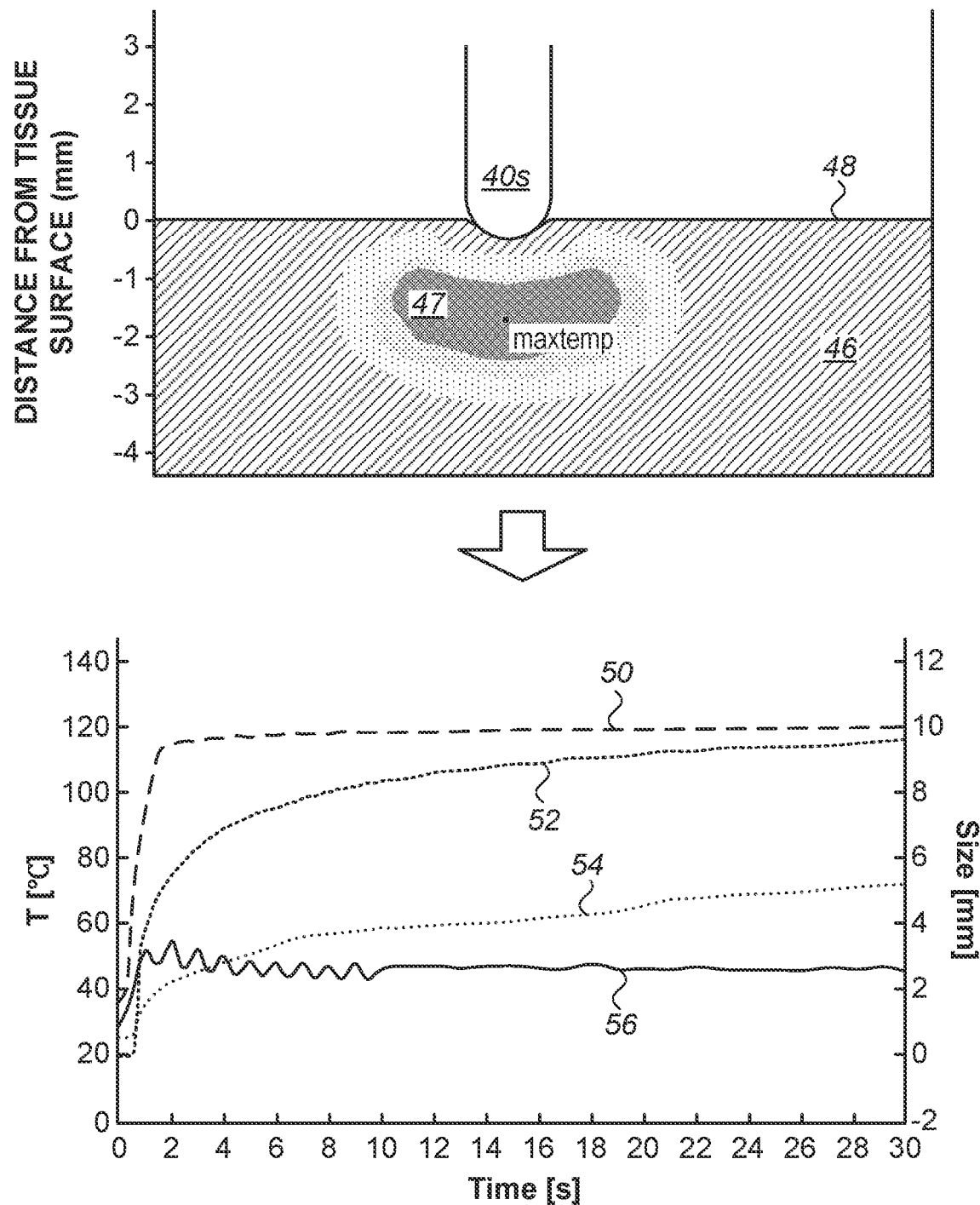
FIG. 3 is a schematic illustration of a simulated ablation used to generate an electric-current profile, in accordance with some embodiments of the present invention.

Reference is now made to FIG. 3, which is a schematic illustration of a simulated ablation used to generate an electric-current profile, in accordance with some embodiments of the present invention.

Typically, processor 36 generates each profile 42 by simulating an ablation, i.e., by simulating the application of an electric current to simulated tissue 46. Such a simulated ablation is depicted pictorially in FIG. 3, whereby a simulated catheter tip 40s applies an electric current to simulated tissue 46 while penetrating the simulated tissue. The various hatch marks beneath the surface 48 of the tissue indicate different respective subsurface temperature ranges, whereby the temperature is highest within a "hot spot" 47, and is progressively lower with distance from hot spot 47. The illustration in FIG. 3 is based on a screenshot of a simulation performed using the Multiphysics® software by COMSOL, Inc. of Burlington, Massachusetts, USA. This software, or any other similar software that models the effect of electric current on biological tissue, may be used to perform the simulations described herein.

While simulating the application of the electric current, the processor monitors the maximum subsurface temperature ("maxtemp") of the simulated tissue (attained within hot spot 47), and controls the amplitude of the electric current responsively thereto, as further described below. Following the simulated ablation, the processor derives a function of time—referred to above as an electric-current profile—from the values of the amplitude over the simulated ablation, and then stores the function of time in memory 32 (FIG. 1) for subsequent use in an ablation procedure, as described above with reference to FIG. 2.

For example, the processor may select at least some of the values of the amplitude over the simulated application, and then store the selected values. In this case, the stored profile includes a time series of amplitude values, i.e., multiple values of the amplitude for different respective times. Alternatively, the processor may fit a predefined function template to the amplitude values, and then store the resulting function. In some embodiments, this template is of the form $(a+t^b)/(c+d*t^e+f*t^g)$ for time t and constants a, b, c, d, e, f, and g. In this case, further to fitting the template to the amplitude values, the processor stores the constants a through g. (As a purely illustrative example, in one case, the inventors obtained a=323.2, b=7.345, c=315.3, d=1.299, e=7.432, f=0.1815, and g=−4.729.)

While simulating the ablation, the processor controls the amplitude of the simulated current such that the maximum subsurface temperature increases toward a predefined temperature threshold (or "limit") $T_{lim}$ (which is 120° C. in FIG. 3), without exceeding the predefined threshold. In particular, the processor may cause the maximum subsurface temperature to quickly (e.g., in less than 1.5 s from the start of the simulated application) increase to within a small margin (e.g., to within 5° C.) of the predefined threshold, and to then remain within this margin until the end of the simulated application. For example, after increasing to within 5° C. of the threshold, the maximum subsurface temperature may continue increasing, e.g., asymptotically, toward the threshold.

Typically, the threshold temperature $T_{lim}$ is between 120 and 130° C. In general, $T_{lim}$ is selected to be as high as possible, provided that there exist a margin of safety with respect to the critical temperature at which the probability of a steam pop forming exceeds a given threshold. (This temperature is described in the aforementioned U.S. Pat. No. 9,241,756 to Berger et al., whose disclosure is incorporated herein by reference.) Thus, for example, if the critical temperature is 125° C., $T_{lim}$ may be 120° C.; as another example, if the critical temperature is 140° C., $T_{lim}$ may be 130° C.

Typically, to cause the maximum subsurface temperature to vary in the manner described above, the processor varies the amplitude of the simulated current in the manner described above with reference to FIG. 2. That is, the processor causes the amplitude to increase rapidly (e.g., in less than 0.5 s) to a maximum value $A_{max}$, and then remain at or below $A_{max}$ until the end of the simulated ablation. More specifically, following the initial increase of the amplitude to $A_{max}$, the processor uses a suitable control function to control the amplitude of the simulated current based on the current maximum subsurface temperature "T." Such a control function may, for example, set the next value of the amplitude as a function of the difference between T and $T_{lim}$, such that, as T approaches $T_{lim}$, the amplitude decreases. For example, given a current value "A" of the amplitude, the next value of the amplitude may be set to min (A, max ($A_{min}$, $|A_{min}-C*(T-T_{lim})|$)), where $A_{min}$ is a predefined minimum amplitude value and C is a predefined constant. (As a purely illustrative example, $A_{min}$ may be 0.4 A for the RMS amplitude, and/or C may be 0.05.)

Typically, prior to the simulated ablation, the processor receives the maximum amplitude $A_{max}$ and the threshold temperature $T_{lim}$ as inputs. In other embodiments, the processor does not receive a specific $A_{max}$ value as an input. Rather, the processor receives a suitable range of values for $A_{max}$ (e.g., 0.8-1.2 A for the RMS amplitude). Subsequently, the processor iteratively selects various $A_{max}$ values from within this range, until a suitable profile is obtained. (It is noted that, typically, there is no specific "optimal" $A_{max}$, since one profile having a larger $A_{max}$ than another profile will also have a shorter plateau at $A_{max}$, such that the two profiles will generally have approximately the same effect on the subsurface temperature of the tissue.)

By way of example, FIG. 3 also shows a first plot 50 of the maximum subsurface temperature over the course of the simulation, in which the maximum subsurface temperature may be seen to increase asymptotically toward the predefined threshold of 120° C. FIG. 3 also shows a second plot 52 of the width of the simulated lesion (in mm) over the course of the simulation, along with a third plot 54 of the depth (in mm) of the simulated lesion. The processor may display these plots to physician 28 (FIG. 1) prior to the actual ablation procedure, so that the physician may ascertain the duration that corresponds to a particular target lesion size. The physician may then apply the ablating current for this duration, such as to achieve the target lesion size. Alternatively, the physician may input the target lesion depth and/or width, and the processor may then apply the ablating current for the duration that achieves the desired target.

FIG. 3 further includes a fourth plot 56 of the surface temperature of tissue 46—i.e., the temperature of the tissue at surface 48—during the simulation. Fourth plot 56 demonstrates that the surface temperature may not be a good indicator for the maximum subsurface temperature.

Typically, the processor performs a different respective set of simulations for each type of ablation catheter. That is, for each type of catheter, the processor performs multiple simulations for various sets of ablation parameters. As described above with reference to FIG. 1, these parameters may include the tissue thickness, contact force, irrigation-fluid flow rate, and/or penetration depth.

In some embodiments, profiles 42 are generated by another processor, rather than by processor 36. Each profile may be stored in any suitable memory, which may be remote from processor 36, prior to being transferred to memory 32. (Alternatively, processor 36 may load the profile directly from the remote memory over any suitable communication interface.) Subsequently, during the ablation procedure, the processor drives current source generator 30 (FIG. 1) to supply an electric current having an amplitude that varies in accordance with the profile, as described above with reference to FIG. 2.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
    a current source generator; and
    a processor, configured to drive the current source generator to supply, for application to tissue of a subject, an electric current having an amplitude that varies in accordance with a predefined function of time, such that the amplitude initially monotonically increases to a maximum value,
    wherein the processor is configured to adjust the amplitude of the electric current responsively to an estimated maximum subsurface temperature after the amplitude reaches the maximum value.

2. The system according to claim 1, wherein the predefined function of time includes a time series of values.

3. The system according to claim 1, wherein the predefined function of time returns, for any value of time t, $(a+t^b)/(c+d*t^e+f*t^g)$ for constants a, b, c, d, e, f, and g.

4. The system according to claim 1, wherein the amplitude is a root mean square (RMS) amplitude, and wherein the maximum value of the RMS amplitude is between 0.8 and 1.2 A.

5. The system according to claim 1, wherein the processor is configured to cause the amplitude to monotonically increase to the maximum value in less than 0.5 s.

6. The system according to claim 1, wherein the processor is further configured to:
during the application of the electric current and following the increase of the amplitude to the maximum value, receive a signal indicating a surface temperature of the tissue, and
in response to the signal, adjust the amplitude of the electric current.

7. The system according to claim 6, wherein the processor is further configured to calculate the estimated maximum subsurface temperature of the tissue from the surface temperature.

8. The system according to claim 6, wherein the processor is further configured to calculate an estimated maximum subsurface temperature of the tissue from the surface temperature, and wherein the processor is configured to adjust the amplitude of the electric current responsively to the estimated maximum subsurface temperature.

9. The system according to claim 1, wherein the electric current is applied to the tissue by a distal tip of a catheter, and wherein the processor is further configured to:
calculate an estimated depth of penetration into the tissue of the distal tip of a catheter, and
select the predefined function of time from multiple predefined functions of time, responsively to the estimated depth of penetration.

10. The system according to claim 1, wherein the predefined function of time includes a time series of values.

11. A method, comprising:
loading, from a computer memory, a predefined function of time;
driving a current source generator to supply, for application to tissue of a subject, an electric current having an amplitude that varies in accordance with the predefined function of time, such that the amplitude initially monotonically increases to a maximum value; and
after the amplitude reaches the maximum value, adjusting the amplitude of the electric current responsively to an estimated maximum subsurface temperature.

12. The method according to claim 11, wherein the predefined function of time includes a time series of values.

13. The method according to claim 11, wherein the predefined function of time returns, for any value of time t, $(a+t^b)/(c+d*t^e+f*t^g)$ for constants a, b, c, d, e, f, and g.

14. The method according to claim 11, wherein the amplitude is a root mean square (RMS) amplitude, and wherein the maximum value of the RMS amplitude is between 0.8 and 1.2 A.

15. The method according to claim 11, wherein the amplitude of the electric current monotonically increases to the maximum value in less than 0.5 s.

16. The method according to claim 11, further comprising:
during the application of the electric current and following the increase of the amplitude to the maximum value, receiving a signal indicating a surface temperature of the tissue; and
in response to the signal, adjusting the amplitude of the electric current.

17. The method according to claim 16, further comprising calculating the estimated maximum subsurface temperature of the tissue from the surface temperature.

18. The method according to claim 11, wherein the electric current is applied to the tissue by a distal tip of a catheter, and wherein the method further comprises:
calculating an estimated depth of penetration into the tissue of the distal tip of a catheter; and
selecting the predefined function of time from multiple predefined functions of time, responsively to the estimated depth of penetration.

19. A system, comprising:
a current source generator; and
a processor, configured to drive the current source generator to supply, for application to tissue of a subject, an electric current having an amplitude that varies in accordance with a predefined function of time, such that the amplitude initially monotonically increases to a maximum value,
wherein the electric current is applied to the tissue by a distal tip of a catheter, and wherein the processor is further configured to:
calculate an estimated depth of penetration into the tissue of the distal tip of a catheter, and
select the predefined function of time from multiple predefined functions of time, responsively to the estimated depth of penetration.

20. The system according to claim 19, wherein the predefined function of time returns, for any value of time t, $(a+t^b)/(c+d*t^e+f*t^g)$ for constants a, b, c, d, e, f, and g.

* * * * *